United States Patent [19]
Stenhagen

[11] Patent Number: 5,376,789
[45] Date of Patent: Dec. 27, 1994

[54] METHOD AND DEVICE FOR LC-SFC/MS INTERFACING

[75] Inventor: Gunnar Stenhagen, Mölndal, Sweden

[73] Assignee: Carlo Erba Strumentazione S.p.A., Milan, Italy

[21] Appl. No.: 872,280

[22] Filed: Apr. 23, 1992

[30] Foreign Application Priority Data

Apr. 24, 1991 [IT] Italy ............... M191 A 001139

[51] Int. Cl.$^5$ .................................................. H01J 49/04
[52] U.S. Cl. ...................................... 250/288; 250/281; 250/282
[58] Field of Search ............... 250/288, 288 A, 282, 250/281; 73/23.2, 864.81, 864.83, 864.84, 864.85, 864.82

[56] References Cited

U.S. PATENT DOCUMENTS

| | | | |
|---|---|---|---|
| 4,641,541 | 2/1987 | Sharp | 250/288 A |
| 4,885,076 | 12/1989 | Smith et al. | 250/288 |
| 5,103,093 | 4/1992 | Sakairi et al. | 250/288 |
| 5,130,538 | 7/1992 | Fenn et al. | 250/288 |
| 5,162,651 | 11/1992 | Kato | 250/288 |
| 5,164,593 | 11/1992 | Chapman et al. | 250/288 |
| 5,170,053 | 12/1992 | Hail et al. | 250/288 |

OTHER PUBLICATIONS

Hans Alborn et al., "Direct Coupling, etc.", *Journal of Chromatography*, 323 (1985) 47–66.

*Primary Examiner*—Paul M. Dzierzynski
*Assistant Examiner*—Kiet T. Nguyen
*Attorney, Agent, or Firm*—Millen, White, Zelano & Branigan

[57] ABSTRACT

A method for interfacing LC or SFC chromatographic equipment with a mass spectrometer, comprises the steps of: positioning at least one conductive element adjacent said column end; positioning said column end and said conductive element at a preselected distance from the mass spectrometer ion source; and connecting said conductive element to a high voltage source and grounding said ion source, or vice versa.

14 Claims, 4 Drawing Sheets

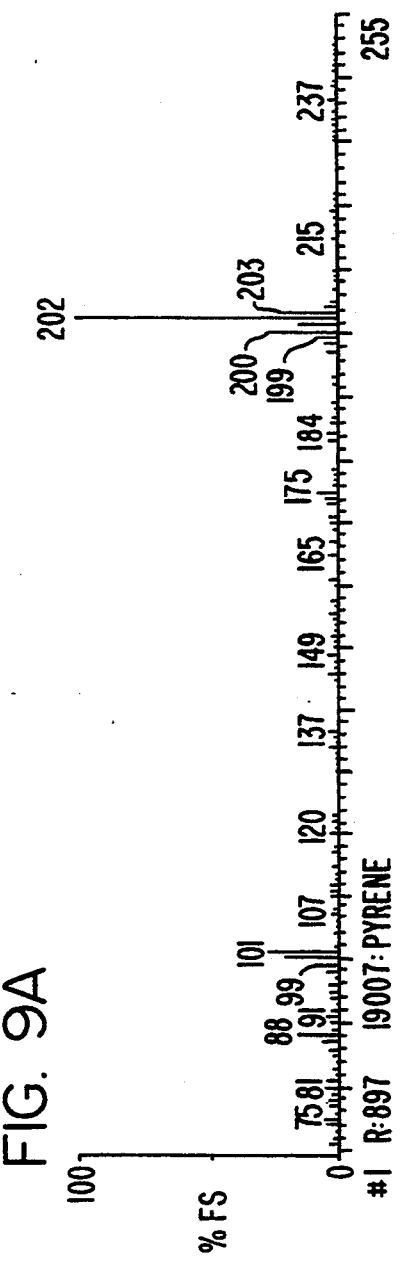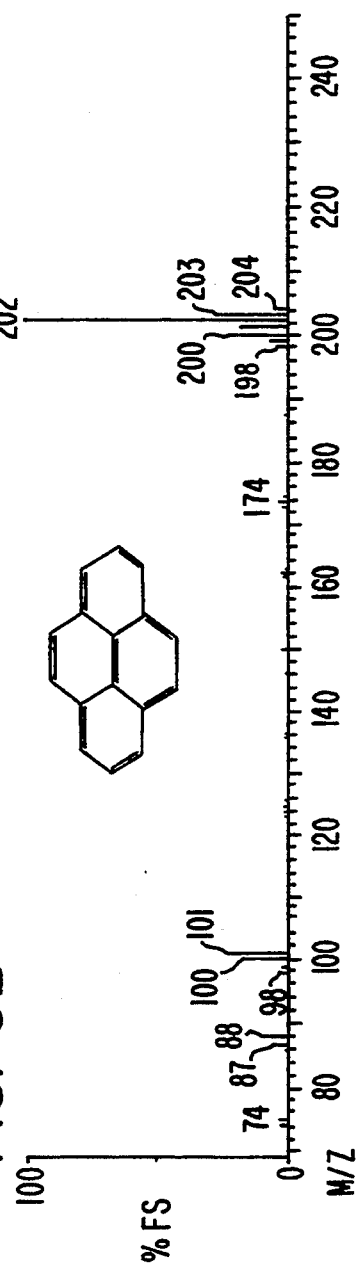
FIG. 9A
FIG. 9B

METHOD AND DEVICE FOR LC-SFC/MS INTERFACING

BACKGROUND OF THE INVENTION

FIELD OF THE INVENTION

The present invention relates to a method and a device for interfacing chromatographic equipment with a mass spectrometer.

More precisely, the present invention relates to a method and a device for interfacing an LC (liquid chromatography) equipment or an SFC (supercritical fluid chromatography) equipment with a Mass Spectrometer (MS) in order that classical electron impact and chemical ionization mass spectra can be obtained.

The main problem to be solved when coupling an LC (or SFC) equipment to a mass spectrometer is to provide eluent to the ion source in a vaporized condition.

According to a first known technique, the eluent exiting the column end of the chromatographic apparatus is heated to provide the required vaporization.

The main drawback of this technique is that it is clearly unsuitable for thermolabile compounds and that it is very difficult to obtain a localized heating at the column tip only, i.e., without affecting the eluent within the upper portion of the column.

Other methods such as thermospray (TS), atmospheric pressure ion evaporation (AIPE) and electrospray (ES) interfaces have been developed for LC/MS in recent years. All of these three techniques nebulize and ionize the column effluent in one step at atmospheric pressure and the ions formed are transported from the high pressure region into the vacuum region of the mass spectrometer for analysis.

In TS, nebulization occurs by passing the sample liquid through a small bore tube whose walls are hot enough to vaporize most of the solvent, while in APIE, the sample is nebulized by a jet of air in the vicinity of a polarizing electrode at high pressure. ES produces atomization by charging. In this method, the sample liquid is injected into a chamber at high pressure through a metal hypodermic needle at a potential of several kilovolts, relative to the surrounding chamber wall. Charge is therefore deposited on the surface of the emerging liquid and disperses the liquid into a fine spray.

In all three above techniques (TS, APIE ES) evaporation of the solvent from the droplets increases the surface charge and decreases the radius of the droplets. The resulting increase in electric field strength eventually reaches levels high enough to desorb ions into the ambient gas. A major drawback of TS, APIE and ES is that ionization specific to each technique is obtained rather than classical electron impact ionization or chemical ionization, i.e., the most widely used ionization techniques.

An alternative technique subsequently developed (H. Alborn and G. Stenhagen; Journal of Chromatography, 323 (1985) 47–66), partially solved these problems under high vacuum conditions of the mass spectrometer.

According to this technique, eluent is nebulized into a fine spray by means of an electrostatic field generated between the column tip and the ion source, that is kept at a high positive voltage, namely about 5 Kv.

In order to avoid the nebulized droplets hitting the ion source outer walls, an extra focusing plate was provided between the column end and the ion source. This plate is held at an intermediate (positive) voltage, e.g., 4 Kv. On entering the ion source, the droplets hit the hot surface of the walls and vaporize, whereupon they are subject to electron impact ionization.

The above disclosed technique has several drawbacks. First, the position of the column end with respect to the focusing plate has to be manually adjusted: to this purpose a glass "window" is located at one side of the mass spectrometer to visually control said adjustment and obtain an optimal conformation of the spray generated through the electrostatic field. This is obviously a time consuming and antieconomical operation.

Secondly, the above cited technique is implementable only on Magnetic Sector mass spectrometers.

Last but not least, said technique required extensive modifications to the said MS equipment.

OBJECTS OF THE INVENTION

An object of the present invention is therefore to solve the above listed drawbacks by means of a method for interfacing LC or SFC chromatography equipment with a mass spectrometer that requires no modifications or very limited modifications of existing spectrometers and may be implemented on different types of spectrometers, besides the magnetic sector one, provided with classical electron impact or chemical ionization.

Another object of the invention is to provide a device for carrying out said method, that is simple and economical to build and is suitable to be used with different types of mass spectrometers.

SUMMARY OF THE INVENTION

Said objectives are achieved by means of the present invention, that provides a method for interfacing an LC or SFC chromatographic equipment with a mass spectrometer comprising the step of nebulizing the eluent exiting the column end by means of an electrostatic field, characterized in that it further comprises the steps of:

- positioning one or more conductive elements adjacent said column end;
- positioning said column end and said conductive element at a preselected distance from the ion source; and
- connecting said conductive elements to a high potential source and grounding said ion source, or vice versa.

The invention also provides a device for interfacing an LC or SFC chromatographic equipment with a mass spectrometer, comprising means to generate an electrostatic field between said column end and the spectrometer ion source to nebulize the eluent exiting the column end, characterized in that it is further comprising:

- at least one conductive element positioned adjacent to the column end;
- means to alternatively connect said conductive element to a high voltage source or to ground them;
- said element and connecting means being at least partially positioned within insulating means located at one end of a guide tube housing the end portion of said chromatographic column.

According to an advantageous embodiment of the invention, said conductive element is located around the chromatographic column outlet and preferably consist of a thin layer of metal directly deposited on the column end. This metal is most preferably gold. Said insulating means, such as teflon or machinable glass, and guide tube housing the end portion of the chromatographic column are advantageously part of a probe that is insertable as a whole unit in the mass spectrometer to act as interfacing means.

According to another advantageous embodiment the actual interface comprises also a focusing plate that is positioned between the column end tip and the ion source. This plate is held at a voltage that has an intermediate value between the conductive element value and the ion source value.

Alternatively, the eluent may be nebulized directly into the evacuated ion source.

The peculiar configuration of the invention device enables its use with different kinds of mass spectrometers. Namely, when used as interfacing means with a magnetic sector MS, the conductive element is grounded and the ion source of the MS is held at a high, usually positive, voltage (e.g., 5 Kv).

When the invention device is used with a quadrupole spectrometer, the MS ion source is grounded or kept at a low potential with respect to the conductive element to which is applied a high, usually positive voltage (e.g. 4 Kv).

The invention will now be further disclosed with reference to the drawings herein enclosed to an illustrative and non limiting purpose, where:

BRIEF DESCRIPTION OF THE DRAWINGS

FIGS. 9(A) and 9(B) are is a comparison of EI and library spectra of a component of FIG. 8 mixture.

DESCRIPTION OF THE PREFERRED EMBODIMENTS

In the following description "column" and "chromatographic column" wording indicates the actual column of the LC or SFC equipment, or a transfer line connected to said actual column.

Both of them are usually provided with a restriction, in a way known in the art.

Similarly, "conductive element" indicates any element to which a high voltage may be applied, or that may be grounded in a way known in the art, "Grounding" means that the element is actually grounded or held at a very low voltage.

Figure 1:
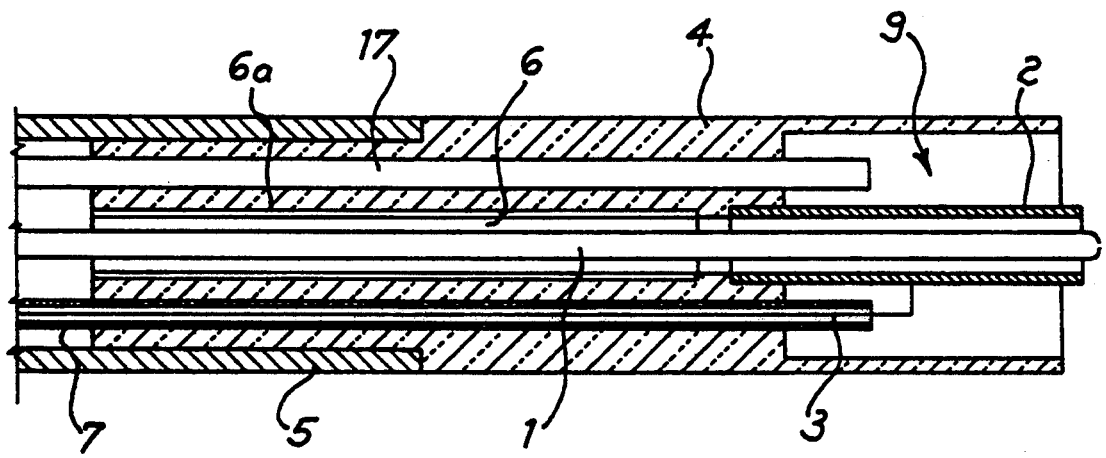
FIG. 1 is an enlarged sectional view of a portion of a preferred invention embodiment.

With reference to FIG. 1, the invention device essentially comprises at least one electrically conductive element 2 positioned close to the end of the column 1. Element 2 is provided with a connector cable 3 or similar connecting means to either ground the conductive element 2 or to connect it to a source of d.c. high voltage (not shown). Element 2 is partially housed within insulating means 4, usually made of teflon, machinable glass or similar insulating material.

Figure 2:
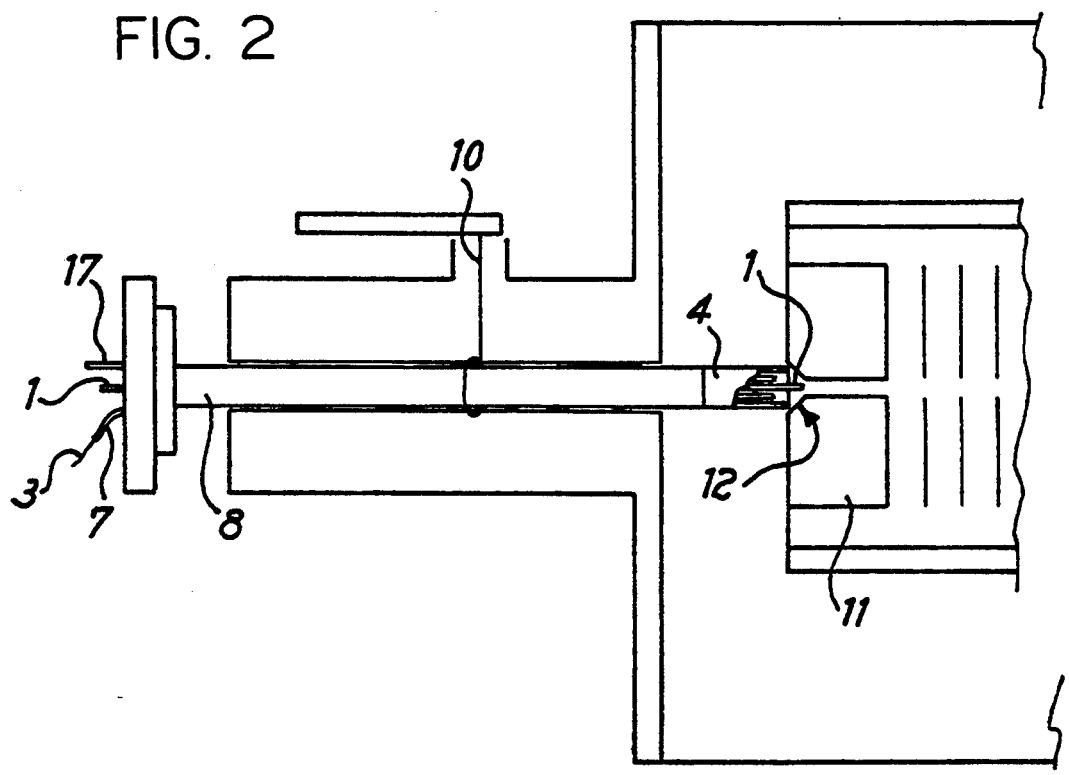
FIG. 2 is a partially sectional view of FIG. 1 embodiment in use.

As disclosed in FIGS. 1 and 2, insulating means 4 are located at the end of a guide tube 5, that is housing column 1 end portion.

Insulating means 4 are provided with a duct 6 housing column 1; preferably column 1 is also housed within an insulating sheath 6a that extends from means 4 inside guide tube 5. A further duct which houses connector cable 3, with an insulating sheath 7, e.g. in teflon, to insulate connector 3 from guide tubes is also provided at upstream means 4.

Conductive element 2 is usually positioned around the actual tip of the column end, that also protrudes from a wide bore portion 9 of insulator 4, i.e. the portion partially housing column 1 end portion and conductive element 2.

In the preferred embodiment shown in FIG. 1 feeding means are provided in the form of a tube 17 that connects portion 9 of insulator 4 with a source of make-up gas, to help in transporting sample into the ion source 11.

In the preferred embodiment of the invention (as in FIG. 2), insulating means 4, guide tube 5 and element 2 are all part of a probe unit 8 that can be interchangeably located at the interface of the MS equipment.

In FIG. 2, probe 8 is inserted through a known vacuum lock 10 and is positioned near ion source 11 in the evacuated area of the MS. In this configuration, the column 1 end is protruding into the ion source inlet 12, and the exiting eluent is nebulized directly into the ion source.

Figure 3:
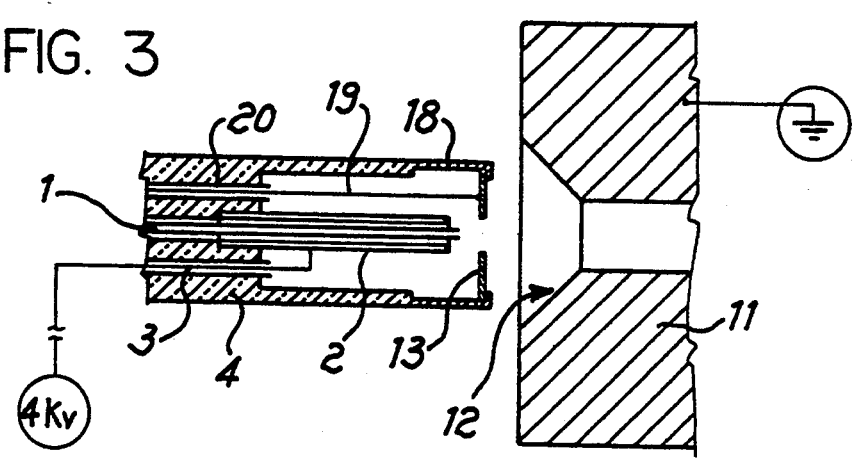
FIG. 3 and 4 are schematical views of two different operating modes of the invention device.
Figure 4:
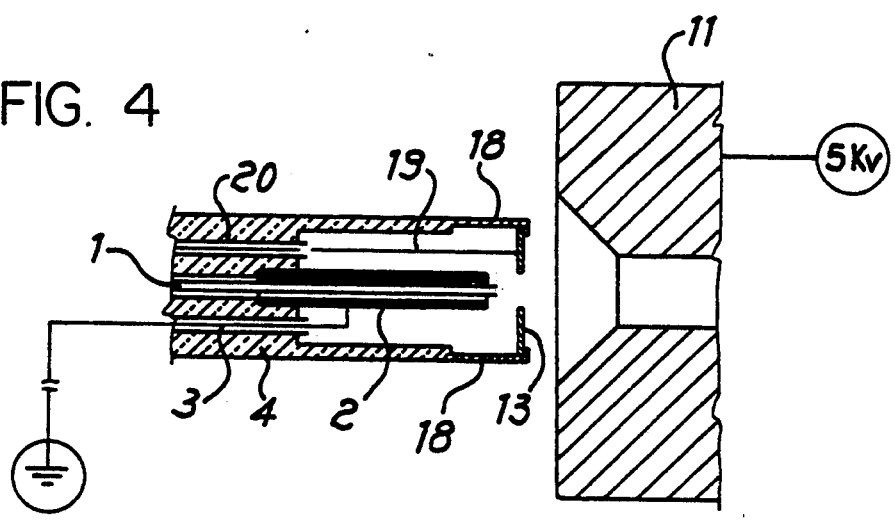

Alternatively, the invention device may also contain a focusing plate 13 located between the end of column 1 and the ion source 11 and preferably mounted onto insulating means 4 by supporting arms 18 thus being part of probe unit 8 (FIGS. 3 and 4). Note that supporting arms 18 prevent the focusing plate touching the source block when it is pushed through the probe lock (see FIGS. 3 and 4).

Plate 13 is provided with a sheathed cable, 19, 20 to connect it with a d.c. power source in order to apply to the said plate 13 a voltage that has a value intermediate between the voltage values of element 2 and of ion source 11. Supporting arms 18 are preferably made of insulating material, e.g. integral with insulator 4.

As previously disclosed, the invention device is suitable for interfacing LC and SFC equipments to a MS spectrometer. In the latter case, i.e., in a SFC-MS interface, heating means (not shown) are preferably provided to neutralize the cooling effect of the eluent expansion at its exit from the column restriction in LC-MS interface cooling means are preferred.

Figure 5:
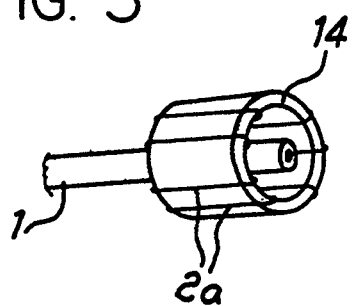
FIG. 5-7 are schematical views of possible different embodiments of the conductive elements of the invention device.
Figure 6:
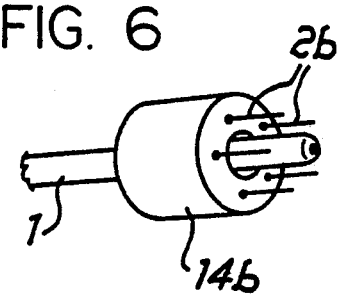
Figure 7:
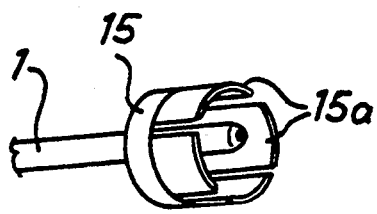

In FIGS. 5-7 are schematically disclosed several different embodiments of the conductive element 2. As shown, besides the tube disclosed in FIG. 1, element 2 may consist of a plurality of windings 2a (FIG. 8), obviously interconnected, wound around an insulating support 14.

Alternatively, element 2 may comprise a plurality of interconnected spikes 2b (FIG. 6) partially housed in supporting means 14b, or finally a circular plate 15 and several tangential plates 15a (FIG. 7).

According to a preferred embodiment (not shown), the conductive element 2 consists of a metal plating, i.e., of a thin layer of metal directly deposited on the column end.

Most preferably the metal used for the conductive element is gold.

In all above disclosed embodiments, the position of the column end will be substantially the same as that shown in FIG. 1, i.e., the column is slightly protruding from the conductive elment(s) and from insulating means 4.

The peculiar configuration of the invention device enables a great flexibility of its use.

According to the invention, the method for interfacing LC or SFC equipment with a mass spectrometer is comprising the steps of positioning at least one conductive element adjacent the column end, locating said column end and the adjacent conductive element 2 at preselected distance from the ion source of the spectrometer, and connecting conductive element 2 to a high voltage source while grounding the ion source 11, or vice versa, to generate the required electrostatic field.

The conductive element 2 is, as above disclosed, usually positioned around and slightly upstream the column end, and the distance of the column end-conductive element from the ion source is preferably very small.

In this case, the interface device as a probe is positioned very near the ion source. The column end is protruding into the ion source inlet 12, and the eluent exiting the column end is nebulized directly into the ion source.

If a traditional configuration is used, i.e., with the column end more distant from the ion source, a focusing plate 13 is preferably positioned between column end and ion source. This plate is held at an intermediate voltage between element 2 and ion source 11 voltage values, to focus the spray of nebulized eluent into the ion source inlet.

As above disclosed, the electrostatic field is generated either by applying a high voltage to the conductive element 2 and grounding ion source 11 (at least, but preferably the whole equipment is grounded) or, vice versa, by grounding element 2 and applying said high voltage to ion source 11.

The first operating mode is schematically disclosed in FIG. 3, and is implemented when interfacing to a quadrupole spectrometer is required. Element 2 potential is preferably about 4 Kv.

The latter operating mode is implemented when interfacing to a magnetic sector spectrometer is required. This case is schematically shown in FIG. 4, where ion source 11 is preferably held at 4–5 Kv, while element 2 is grounded or held at a very low voltage.

In both cases, ionization may be obtained by classical and widely used techniques of electron impact or chemical ionization.

The invention will be further disclosed hereinafter by means of the following, non-limiting, example.

EXAMPLE I

Figure 8:
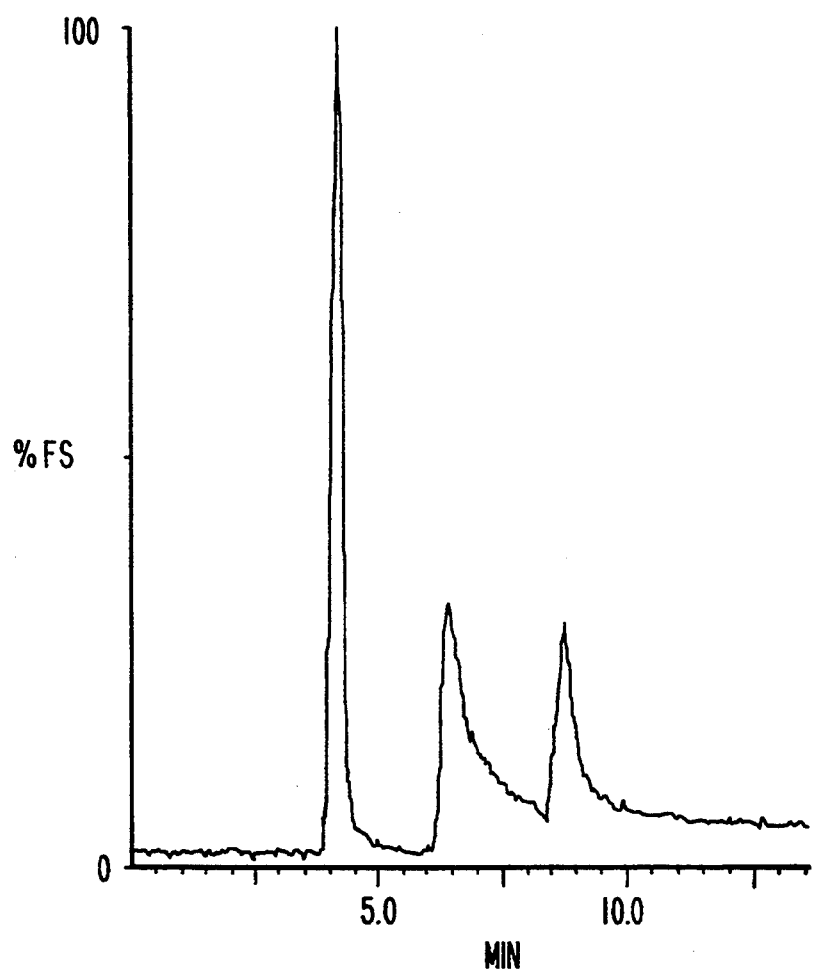
FIG. 8 is a total ion chromatogram of a LC/MS separation of a mixture of polycyclic aromatic hydrocarbons.

Micro LC/MS analysis of a mixture of polycyclic aromatic hydrocarbons. The relevant total ion chromatogram of separation is shown in FIG. 8.

LC CONDITIONS:
  Column, 15 cm×0.22 um fused silica packed with 5 um C18 HPLC material
  Eluent, 80% methanol/20% $H_2O$
  Flowrate, 5 ul/min.

PROBE CONDITIONS:
  Probe as shown in FIGS. 1 and 2 was used.
  Conductive element 2 at 3.5 KV source was grounded.
  Source temperature 180 C.
  No make up gas used.

MS CONDITIONS:
  Quadrupole mass spectrometer, mass range 2–1000 amu, Electron impact source at 70 ev.

EI mass spectrum (A) of third eluting component obtained from acquisition shown in FIG. 1 (pyrene), and comparison with EI library spectrum of pyrene (B) are shown in FIG. 9. This was the first spectrum selected on performing library searching of NIST Electron Impact library of 50000 compounds with a search score of 897/1000.

The previously referred to apparatuses for conducting LC-MS or SFC-MS analyses, provided with an interfacing device according to the present invention, are obviously a further object of the invention.

I claim:

1. A method for interfacing LC or SFC chromatographic equipment with a mass spectrometer ion source, comprising the step of nebulizing the eluent exiting an equipment column end by means of an electrostatic field, wherein the method further comprises the steps of:
  positioning in a vacuum a conductive element adjacent said column end;
  positioning in said vacuum said column end into an inlet of the mass spectrometer ion source; and
  connecting one of said conductive element and said mass spectrometer ion source to a high voltage source and the other to ground to generate said electrostatic field in said vacuum.

2. A method according to claim 1, further including the steps of positioning a focusing plate between said column end and said mass spectrometer ion source and applying to said focusing plate an intermediate voltage to focus the nebulized eluent spray.

3. A method according to claim 1, wherein said mass spectrometer ion source (11) cooperates with a magnetic sector spectrometer, and wherein there is grounding of said conductive element (2) and application of a high potential to said mass spectrometer ion source (11).

4. A method according to claim 1, wherein said mass spectrometer ion source cooperates with a quadrupole spectrometer and where there is grounding of said mass spectrometer ion source (11) and application of a high potential to said conductive element.

5. A method according to claim 1, wherein said eluent is nebulized directly into the mass spectrometer ion source.

6. A device for interfacing an LC or SFC chromatographic equipment with a mass spectrometer ion source, comprising a vacuum chamber and means for generating an electrostatic field between an equipment column end and the mass spectrometer ion source in said vacuum chamber to nebulize the eluent exiting the column end and further comprising:
  at least one conductive element positioned adjacent to the column end in the vacuum chamber; and
  means for alternatively connecting one of said conductive elements and said mass spectrometer ion source to a high voltage source and the other to ground to generate said electrostatic field in said vacuum chamber;
  wherein said conductive element and said connecting means being at least partially positioned within insulating means located at one end of a guide tube housing an end portion of said chromatographic column end and the other end portion of said chromatographic column end is protruding into an inlet of said mass spectrometer ion source.

7. A device according to claim 6, further comprising a focusing plate located between said column end and said mass spectrometer ion source, said focusing plate being provided with connecting means to connect the focusing plate to a source of an intermediate voltage.

8. A device according to claim 7, wherein said guide tube, said insulating means and said focusing plate are part of a probe unit.

9. A device according to claim 6, wherein said conductive element is located upstream and around said column end, and said column end is protruding from the insulating means.

10. A device according to claim 6, wherein said mass spectrometer ion source is a magnetic sector mass spectrometer, said conductive element is grounded and said mass spectrometer ion source is connected with a high voltage source.

11. A device according to claim 6, wherein said mass spectrometer ion source (11) cooperates with a magnetic sector mass spectrometer, wherein said conductive element (2) is grounded and said mass spectrometer ion source (11) is connected with a high voltage source.

12. A device according to claim 6, wherein said mass spectrometer ion source (11) cooperates with a quadrupole mass spectrometer, wherein said conductive element (2) is connected to a high voltage source and said mass spectrometer ion source (11) is grounded.

13. A device according to claim 6, wherein said conductive element is made of gold.

14. A device according to claim 6 comprising further feeding means for adding a gas to near the eluent exiting from the column end.

* * * * *